United States Patent
Greenbaum et al.

(10) Patent No.: US 10,369,178 B2
(45) Date of Patent: Aug. 6, 2019

(54) TOBACCO PRODUCTS WITH CANNABINOID ADDITIVES AND METHODS FOR REDUCING THE HARM ASSOCIATED WITH TOBACCO USE

(71) Applicant: Resurgent Pharmaceuticals, Inc., Minneapolis, MN (US)

(72) Inventors: Eric Greenbaum, New York, NY (US); Kyle Kingsley, Minneapolis, MN (US)

(73) Assignee: Resurgent Pharmaceuticals, Inc., Minneapolis, MN (US)

( * ) Notice: Subject to any disclaimer, the term of this patent is extended or adjusted under 35 U.S.C. 154(b) by 0 days.

(21) Appl. No.: 15/451,377

(22) Filed: Mar. 6, 2017

(65) Prior Publication Data
US 2019/0022158 A1     Jan. 24, 2019

Related U.S. Application Data

(60) Provisional application No. 62/304,276, filed on Mar. 6, 2016.

(51) Int. Cl.
| | | |
|---|---|---|
| A61K 36/00 | (2006.01) | |
| A61K 36/185 | (2006.01) | |
| A61K 31/047 | (2006.01) | |
| A61K 31/352 | (2006.01) | |
| A24D 3/14 | (2006.01) | |
| A24B 3/12 | (2006.01) | |
| A24B 15/30 | (2006.01) | |
| A24D 1/00 | (2006.01) | |

(52) U.S. Cl.
CPC .............. *A61K 36/185* (2013.01); *A24B 3/12* (2013.01); *A24B 15/302* (2013.01); *A24B 15/303* (2013.01); *A24D 1/002* (2013.01); *A24D 3/14* (2013.01); *A61K 31/047* (2013.01); *A61K 31/352* (2013.01); *A61K 2236/37* (2013.01); *A61K 2236/39* (2013.01)

(58) Field of Classification Search
CPC ..................................................... A61K 36/00
USPC ........................................................ 424/725
See application file for complete search history.

(56) References Cited

U.S. PATENT DOCUMENTS

2017/0172977 A1*   6/2017   Kleidon ............... A61K 31/352

* cited by examiner

*Primary Examiner* — Michael V Meller
(74) *Attorney, Agent, or Firm* — Billion & Armitage; John F. Klos

(57) ABSTRACT

A substantially pure fraction of at least one cannabinoid is added to smokable or smokeless tobacco products to reduce the harm associated with tobacco use. The harm to be reduced includes irritation and carcinogenicity of tobacco. In a preferred embodiment a whole plant cannabis extract is mixed directly with the tobacco during the curing or manufacturing process. For cigarette applications the cannabinoids may be inserted into a cigarette filter, and/or paper. In other embodiments the cannabinoids are purified.

3 Claims, No Drawings

TOBACCO PRODUCTS WITH CANNABINOID ADDITIVES AND METHODS FOR REDUCING THE HARM ASSOCIATED WITH TOBACCO USE

STATEMENT REGARDING FEDERALLY SPONSORED RESEARCH

N/A

FIELD OF THE INVENTION

The present invention relates to tobacco products such as cigarettes, cigars, pipe tobacco (bulk), roll your own, and smokeless tobacco products also known as "snuff," "chewing tobacco," and "dipping tobacco." More particularly, novel forms of tobacco and tobacco products including, cured and uncured leaves, which include as additives one or more cannabinoids as health enhancing, harm reduction, and/or experience enhancing agents.

BACKGROUND OF THE INVENTION

Health problems associated with cigarette smoking, cigar smoking, pipe smoking and smokeless tobacco have been well publicized. In various scientific studies, cigarette smoking, cigar smoking, pipe smoking and use of smokeless tobacco have been causally linked to diseases such as lung, throat, mouth and other cancers as well as emphysema, smoker's cough and heart disease.

Various attempts have been made to address cigarette health problems through reformulation of cigarettes. For example, special blends of tobacco have been formulated for cigarettes with reduced levels of tar and nicotine. Unfortunately, each reduction of the tar and nicotine level has been accompanied by a corresponding reduced level of user satisfaction requiring unhealthy longer, stronger puffs to increase smoker's satisfaction. As such, sales of lowered tar and nicotine cigarettes, particularly those commercially classified as "ultra low tar and nicotine", have not lived up to expectations. More recently, efforts have been made to altogether remove additives from cigarettes. While such "additive free" cigarettes may provide a purer tobacco smoke, it is unclear whether they provide any corresponding health benefits. In fact, in some cases, they have been shown to be stronger in tar and nicotine since they contain relatively more tobacco than non-additive containing cigarettes.

SUMMARY OF THE INVENTION

As specified in the Background Section above, there is a need in the art to develop new tobacco additives to reduce the harm associated with tobacco use and improve user experience with tobacco.

Thus According to a first aspect of the present invention there is provided an effective technique for adding cannabinoids to cigarettes, cigars, bulk tobacco (including leaves), reconstituted tobacco, pipe tobacco and smokeless snuff, "moist snuff" or "chewing" tobacco (as smokeless tobacco is commonly known) as well as to non-tobacco smokable and mouthable products. In an embodiment the cannabinoid added to the tobacco is (tetrahydrocannbinol) THC. In another embodiment, the cannabinoid is cannabidiol (CBD). In another embodiment the cannabinoid is selected from the group consisting of tetrahydrocannabinolic acid (THCA), Cannabidiolic acid (CBDA), cannabinol (CBN), cannabigerol (CBG), cannabichromene (CBC), tetrahydrocannabivarin (THCV), and cannabidivarin (CBDV). In another embodiment the cannabinoid is a combination of two or more of the cannabinoids listed herein.

According to a second aspect the invention there is provided a tobacco product selected from the group consisting of cigarettes, cigars, bulk tobacco (including leaves), reconstituted tobacco, pipe tobacco and smokeless snuff or "chewing" tobacco (as smokeless tobacco is commonly known) as well as to non-tobacco smokable and mouthable products, further comprising the addition of one or more cannabinoids selected from the group consisting of tetrahydrocannabinol (THC), cannabidiol (CBD), tetrahydrocannabinolic acid (THCA), Cannabidiolic acid (CBDA), cannabinol (CBN), cannabigerol (CBG), cannabichromene (CBC), tetrahydrocannabivarin (THCV), and cannabidivarin (CBDV).

According to a third aspect of the invention there is provided a method for reducing the harm associated with tobacco use in a subject in need thereof comprising the steps of providing to that user a tobacco product further comprising the addition of one or more cannabinoids selected from the group consisting of tetrahydrocannabinol (THC), cannabidiol (CBD), tetrahydrocannabinolic acid (THCA), Cannabidiolic acid (CBDA), cannabinol (CBN), cannabigerol (CBG), cannabichromene (CBC), tetrahydrocannabivarin (THCV), and cannabidivarin (CBDV).

Preferred features of the invention will now be described in further detail. Features described as being preferred in relation to one aspect of the invention apply mutatis mutandis to all other aspects, unless clearly stated otherwise.

The cannabinoids used may be isolated using any methods known by those having skill in the art, including the use of hydrocarbon solvents and solventless extraction. Therefore in one embodiment the cannabinoids used as additives are produced by extraction of cannabis plant material with supercritical or subcritical $CO_2$. In an alternative embodiment the cannabinoid additives are produced by extraction from plant material by volatilisation with a heated gas. In an alternative embodiment the cannabinoid additives are produced from plant material through the sequential processes of $CO_2$ extraction followed by fractional distillation. In some embodiments, the cannabinoid additives contain all of the naturally occurring cannabinoids in the plant material. Alternatively, synthetic or highly purified isolates of the cannabinoids can be used.

The term "approximately equal" is used to refer to ratios of cannabinoids which are in the range of between 0.9:1 to 1:0.9 (THC:CBD). Additionally the term "1:1" is taken herein to refer to approximately equal amounts of cannabinoids.

DETAILED DESCRIPTION

These and other systems, methods, objects, features, and advantages of the present disclosure will be apparent to those skilled in the art from the following detailed description of the embodiments and drawings.

All documents mentioned herein are hereby incorporated in their entirety by reference. References to items in the singular should be understood to include items in the plural, and vise versa, unless explicitly stated otherwise or clear from the text. Grammatical conjunctions are intended to express any and all disjunctive and conjunctive combinations of conjoined clauses, sentences, words, and the like, unless otherwise stated or clear from context The cannabinoids are a class of molecules primarily obtained through the extraction of cannabis plant material.

The various cannabinoids include tetrahydrocannabinol (THC), cannabidiol (CBD), tetrahydrocannabinolic acid (THCA), Cannabidiolic acid (CBDA), cannabinol (CBN), cannabigerol (CBG), cannabichromene (CBC), tetrahydrocannabivarin (THCV), and cannabidivarin (CBDV) as well as others. Various cannabinoids, used alone or in combination have shown a variety of significant biological effects including but not limited to pain relief, anti cancer, anti inflammatory, anti emetic, anti convulsant, and several others.

With respect to cannabinoid additives for tobacco, CBD is particularly useful due to its non-intoxicating, antineoplastic, anti-inflammatory, and pain relieving effects. While specific embodiments of tobacco products including cannabinoids are discussed with respect to CBD, it is noted that other cannabinoids may be added to or substituted depending on the specific effects desired from the additives. Therefore, in an embodiment, a substantially pure, dry powder of CBD is mixed directly with the tobacco used in smokable or smokeless tobacco during the manufacturing process and/or directly into smokable or smokeless tobacco products. CBD can also be inserted or mixed into mixtures of lamina tobaccos, reconstituted tobacco and lamina tobacco mixed with reconstituted tobacco as well as into a cigarette filter, holder, paper or wrapper. One may also place the additive in tobacco prior to curing so long as it will remain stable enough to sustain its benefits all the way through processing and in storage. Other forms of cannabinoid additives, namely oils can be used in the present invention. Oils may be particularly useful do the fact that it is difficult to get substantially pure, solid forms of many cannabinoids. Oils may be particularly useful in chewing tobacco, and as a coating for the interior surface of cigarette and cigar wrappers. Other formulations of cannabinoids may be incorporated into tobacco products such as microencapsulated, particleized cannabinoids.

Cannabinoids can be incorporated into a tobacco or non tobacco product in a number of different ways including being directly mixed with the tobacco or inserted into a cigarette/cigar filter, holder, or wrapper either in a dry, oil, or microencapsulated form. In an embodiment of the present invention, a substantially pure, "dry" form of CBD can be blended into, sprayed or dusted onto the full or cut tobacco or non-tobacco leaves during the curing or manufacturing process. In that way, the substantially pure, "dry" form of CBD will already be incorporated onto the tobacco when it is rolled into the cigarette packaged in a bulk smokeless container. While the quantity of CBD to be used in this process can vary, it is expected that between 0.1 and 5000 milligrams of CBD or other cannabinoid would be a suitable amount for a cigarette or smokeless tobacco wad containing 400-1200 milligrams of tobacco, with a more preferred amount of CBD or other cannabinoid to be between 0.1% to 20.0% by weight of tobacco or 0.4 milligrams to 240 milligrams for a cigarette or smokeless tobacco wad containing 400-1200 milligram of tobacco. In some embodiments the cannabinoids are added by adding an amount of a whole plant cannabis extract.

In another embodiment the tobacco and cannabinoid additives are provided as a kit comprising separate portions of tobacco and cannabinoid extracts, enabling users to combine the tobacco and cannabinoid additives in proportions of their choosing.

In another embodiment, the cannabinoid(s) are incorporated into the cigarette filter either as dispersed particles, liquid infused into the filter medium or microencapsulated particles. The cannabinoid(s) may also be incorporated into tobacco paper, plug wrap, and or filter paper.

In other embodiments, the cannabinoid(s) are added to the tobacco after the tobacco has been dried, cured and otherwise processed to be ready for formulation into cigarettes, smokeless and other forms. The addition of cannabinoids at this stage is beneficial as it avoids the possibility of degradation of the cannabinoids over time and during the processing steps of the raw tobacco leaves. It also has the added benefit of enabling a more accurate and precise dosage of cannabinoid(s).

In some embodiments terpenes, either alone or in combination with cannabinoids are added as additives to the tobacco products.

In some embodiments the cannabinoids present as additives are THC and CBD present in ratios in the range of 1:100 to 100:1, particularly between 1:20 to 20:1. In some embodiments the cannabinoids present are THC and CBD in a 1:1 ratio.

There are several benefits associated with cannabinoid additives to tobacco products, especially as a harm reduction measure. One benefit is the reduced irritation associated with tobacco product use. In particular, the addition of CBD, with its known anti inflammatory and pain relieving properties is particularly beneficial in reducing some of the discomfort associated with tobacco use. The use of THC as an additive to tobacco products is beneficial, especially in states where the recreational use of cannabis is permitted and as a way to reduce the nausea that sometimes accompanies tobacco use.

The use of cannabinoids as tobacco additives, may be particularly useful as a mechanism to reduce the carcinogenicity associated with tobacco products. Substantial evidence has been presented that these compounds can reduce tumor growth in animal models of cancer. A large body of scientific evidences strongly support THC and other cannabinoid agonists exert anticancer actions in preclinical models of cancer (including immunocompetent mice) through a well-established mechanism of action. See ie *The Use of Cannabinoids as Anticancer Agents*—Velasco et al. Progress in Neuro-Psychopharmacology and Biological Psychiatry, Jan. 4 2016, which is hereby incorporated by reference in its entirety.

The use of cannabinoids as tobacco additives, may be particularly useful as a mechanism to reduce the inflammatory response often caused by the use of tobacco products. Tobacco use is known to cause various inflammatory responses including but not limited to inflammation and irritation of the mouth and throat. Various cannabinoids are known to have an anti-inflammatory effect. See ie *Comparative topical anti-inflammatory activity of cannabinoids and cannbivarins*—Tubaro et al. Fitoterapia, (2010) 816-819, which is hereby incorporated by reference in its entirety.

Therefore, In one embodiment, the invention is a smokable or non smokable composition comprising tobacco and at least one additive selected from the group consisting of tetrahydrocannabinol (THC), cannabidiol (CBD), tetrahydrocannabinolic acid (THCA), Cannabidiolic acid (CBDA), cannabinol (CBN), cannabigerol (CBG), cannabichromene (CBC), tetrahydrocannabivarin (THCV), and cannabidivarin (CBDV).

Another embodiment is, method of reducing the harm associated with tobacco use comprising providing tobacco users with tobacco products to which have been added at least one cannabinoid selected from the group consisting of tetrahydrocannabinol (THC), cannabidiol (CBD), tetrahydrocannabinolic acid (THCA), Cannabidiolic acid (CBDA), cannabinol (CBN), cannabigerol (CBG), cannabichromene (CBC), tetrahydrocannabivarin (THCV), and cannabidivarin (CBDV). In some cases the harm associated with tobacco use that is to be reduced is the inflammation that is associated with tobacco use. In some cases the harm associated with tobacco use that is to be reduced is the carcinogenicity of tobacco. In some cases the harm associated with tobacco used that is to be reduced is the mouth discomfort associated with the use of smokeless tobacco.

Another embodiment is a tobacco mixture with a reduced carcinogenicity profile comprising tobacco with a cannabinoid additive selected from the group consisting of tetrahydrocannabinol (THC), cannabidiol (CBD), tetrahydrocannabinolic acid (THCA), Cannabidiolic acid (CBDA), cannabinol (CBN), cannabigerol (CBG), cannabichromene (CBC), tetrahydrocannabivarin (THCV), and cannabidivarin (CBDV).

Another embodiment is method for reducing free radical damage to the oro-pharyngeal cavity, respiratory tract and lungs from tobacco smoke, the method comprising adding a cannabinoid additive to tobacco products, the additive selected from the group consisting of tetrahydrocannabinol (THC), cannabidiol (CBD), tetrahydrocannabinolic acid (THCA), Cannabidiolic acid (CBDA), cannabinol (CBN), cannabigerol (CBG), cannabichromene (CBC), tetrahydrocannabivarin (THCV), and cannabidivarin (CBDV).

Another embodiment is a cigarette comprising a paper wrapper surrounding a charge of tobacco, said cigarette further comprising a composition for reducing free radical damage to the oro-pharyngeal cavity, respiratory tract and lungs from tobacco smoke generated by said cigarette, said composition comprising a cannabinoid additive to tobacco products, the additive selected from the group consisting of tetrahydrocannabinol (THC), cannabidiol (CBD), tetrahydrocannabinolic acid (THCA), Cannabidiolic acid (CBDA), cannabinol (CBN), cannabigerol (CBG), cannabichromene (CBC), tetrahydrocannabivarin (THCV), and cannabidivarin (CBDV).

While the present disclosure includes many embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

With respect to the above, it is to be understood that the invention is not limited in its application to the details of construction and to the arrangement of the components listed or the steps set forth in the description or illustrated in the drawings. The various apparatus and methods of the disclosed invention are capable of other embodiments, and of being practiced and carried out in various ways that would be readily known to those skilled in the art, given the present disclosure. Further, the terms and phrases used herein are for descriptive purposes and should not be construed as in any way limiting.

As such, those skilled in the art will appreciate that the conception upon which this disclosure is based may be utilized as a basis for designing other inventions with similar properties. It is important therefore that the embodiments, objects, and claims herein, be regarded as including such equivalent construction and methodology insofar as they do not depart from the spirit and scope of the present invention.

What is claimed is:

1. A method for reducing the harmful effects of tobacco use in a human in need thereof consisting essentially of administering to the human in need thereof tobacco and a microencapsulated highly purified isolate of a cannabinoid from cannabis to effectively reduce the harmful effects of tobacco use in the human in need thereof, wherein said cannabinoid is selected from the group consisting of tetrahydrocannabinol, cannabidiol and mixtures thereof.

2. The method of claim 1, wherein tetrahydrocannabinol and cannabidiol are present in a ratio of about 1:20, tetrahydrocannabinol: cannabidiol, when used as a mixture.

3. The method of claim 1, wherein said tobacco is in a form selected from the group consisting of cigarettes, cigars, chewing tobacco, and moist snuff.

* * * * *